United States Patent [19]
Schulze et al.

[11] Patent Number: 5,749,898
[45] Date of Patent: May 12, 1998

[54] SUTURE CARTRIDGE ASSEMBLY FOR A SURGICAL KNOT

[75] Inventors: Dale R. Schulze, Lebanon, Ohio; Troy A. McMillen, Champaign, Ill.

[73] Assignee: Ethicon Endo-Surgery, Inc., Cincinnati, Ohio

[21] Appl. No.: 841,962

[22] Filed: Apr. 8, 1997

[51] Int. Cl.[6] ..................................... A61B 17/04
[52] U.S. Cl. ........................ 606/228; 606/148; 606/139
[58] Field of Search ................... 606/228, 139, 606/148; 289/1.2, 12, 17; 112/80.03, 169

[56] References Cited

U.S. PATENT DOCUMENTS

| | | | |
|---|---|---|---|
| 2,012,776 | 8/1935 | Roeder | 128/326 |
| 2,566,625 | 9/1951 | Nagelmann | 128/326 |
| 3,090,386 | 5/1963 | Curtis | 126/334 |
| 5,217,470 | 6/1993 | Weston | 606/148 |
| 5,242,452 | 9/1993 | Inoue | 606/108 |
| 5,320,629 | 6/1994 | Noda et al. | 606/139 |
| 5,336,231 | 8/1994 | Adair | 606/148 |
| 5,405,352 | 4/1995 | Weston | 606/148 |
| 5,454,821 | 10/1995 | Harm et al. | 606/148 |
| 5,466,241 | 11/1995 | Leroy et al. | 606/139 |
| 5,472,446 | 12/1995 | De La Torre | 606/148 |
| 5,527,323 | 6/1996 | Jervis et al. | 606/148 |
| 5,536,273 | 7/1996 | Lehrer | 606/139 |
| 5,562,684 | 10/1996 | Kammerer | 606/139 |
| 5,573,286 | 11/1996 | Rogozinski | 289/12 |

FOREIGN PATENT DOCUMENTS 912619  4/1994  Germany.

OTHER PUBLICATIONS

Raoul Graumont, John Hensel "Enclyclopedia of Knots and Fancy Rope Work" Plates 30–49.

Howard T. Sharp, M.D., James H. Dorsey, M.D., John D. Chovan, Ph.D., P.E., Patrice M. Holtz, R.N. "A Simple Modification to Add Strength to the Roeder Knot" pp. 305–307 Feb., 1996, vol. 3, No.2 from *The Journal of the American Associates of Gynecologic Laparoscopists*.

Mike Kozminski, M.D., William H. Richards, III, M.D. "Fly–Casting Method of Intracorporeal Laparoscopic Knot Tying", pp. 577–578, from *Urology®*, Oct. 1994, vol. 44, No. 4.

J. L. Pennings, T. Kenyon, L. Swanstrom "The knit stich" from *Surgical Endoscopy* (1995) 9:537–540.

Harry Reich, M.D., H. Courtenay Clarke, M.D., Lisa Sekel, CST "Instruments & Methods", from *Obstet Gynecol* 1992;79:143–147.

Nathaniel J. Soper, M.D., FACS, and John G. Hunter, M.D., FACS "Suturing and Knot Tying In Laparoscopy" *Surgical Clinics of North America*,Oct. 1992 pp. 1139–1153.

S. Kitano, M.D., T. Yoshida, M.D., T. Bandoh, M.D., K. Shuto, M.D., K. Nakashima, M.D. & M. Kobayashi, M.D., "Knot tying intracorporeally at laparoscopic surgery facilitated with newly designed forceps" © 1996 *Blackwell Science Ltd*.

(List continued on next page.)

*Primary Examiner*—Michael Buiz
*Assistant Examiner*—Tina T. D. Pham
*Attorney, Agent, or Firm*—Matthew S. Goodwin

[57] ABSTRACT

A Suture cartridge assembly is disclosed. The cartridge assembly has a partially tied surgical knot formed from a suture filament for facilitating the fastening of body tissue. It also has a core tube to which the partially tied knot is secured. Further, the assembly has a suture cartridge which contains a tube slot for receiving the core tube. The assembly makes it easier to convert the partially tied surgical knot into a non-slip knot to securely and consistently fasten tissue. It is simple in construction, and it is readily adaptable to inclusion on various surgical instruments. When a first partially tied surgical knot is converted to a completed knot, the completed knot and its core tube can be removed from the cartridge, and a second partially tied knot secured about a new core tube can be received into the suture cartridge to enable multiple knot placements.

9 Claims, 9 Drawing Sheets

OTHER PUBLICATIONS

Howard T. Sharp, M.D., James H. Dorsey, M.D., John D. Chovan, Ph.D., P.E., Patrice M. Holtz, R.N., M.S. "The Effect of Knot Geometry on the Strength of Laparoscopic Slip Knots", *Obstetrics & Gynecology*, 1996, pp. 88:408–411.

John E. Meilahn, M.D., "The Need for Improving Laparoscopic Suturing and Knot–Tying", *Journal of Laparoendoscopic Surgery*, vol. 2, No. 5, 1992, pp. 267–268.

D.D. Gaur M.S. FRCS(Eng), "Manual laparoscopic suturing and knot tying made easy", ©1996 Blackwell Science Ltd, pp. 29–33.

Resad Pasic, M.D., Ph.D., Ronald L. Levine, M.D., "Laparoscopic Suturing and Ligation Techniques", Nov. 1995, vol. 3, No. 1 *The Journal of the American Association of Gynecologic Laparoscopists*, pp. 67–79.

Sung–Tao Ko and Mohan C. Airan, "Therapeutic laparoscopic suturing techniques", *Surgical Endoscopy*, (1992)6:41–46.

Zoltan Szabo, Ph.D., FICS, and George Berci, M.D., FACS, FRCS Ed (Hon), "Extracorporeal and Intracorporeal Knotting and Suturing Techniques" *Gastrointestinal Endoscopy Clinics of North America*, pp. 367–373.

SUTURE CARTRIDGE ASSEMBLY FOR A SURGICAL KNOT

BACKGROUND OF THE INVENTION

This invention relates to an assembly for facilitating the placement of a surgical knot made from a suture filament. In particular, the invention relates to such an assembly which is particularly adapted for deployment of the knot during minimally invasive surgical procedures where access to the surgical site is limited.

A mainstay of surgical practice has been and will continue to be the formation and placement of surgical knots from suture filament to fasten tissue during an operative procedure. Numerous surgical knots have been developed over an appreciable period of time, and the art of forming and tying knots for surgical applications is a critical skill which a surgeon must possess to perform an operation safely and efficiently. Accordingly, the art is extensively developed. See, for example, Tissue Approximation in Endoscopic Surgery, Alfred Cuschieri, Zoltan Szabo, Times Mirror International Publishers, 1995, which describes numerous surgical knots made from suture filament to facilitate the approximation of tissue during surgery.

The art of surgical knots is also well represented in the patent literature. U.S. Pat. No. 2,012,776 discloses a surgical instrument for facilitating the placement of various forms of slip knots made from surgical filament. The inventor named on the '776 patent, H. A. Roeder, developed the "Roeder Knot" which is a surgical knot which is frequently used in practice today. More recently, U.S. Pat. No. 5,573,286 discloses a surgical knot of suture strand particularly adapted for orthopedic applications. The preferred embodiment described in the '286 patent is directed to tying the knot to a bone.

Early on, it was recognized that the deployment and placement of surgical knots within a remotely accessible surgical site could be difficult, cumbersome and often unreliable. Accordingly, instrumentation was developed to facilitate the placement of knots in remote locations. Cleverly, a pre-tied knotted loop of suture was often used to reduce the number of steps required to form the tightened knot. For example, U.S. Pat. Nos. 2,566,625 and 3,090,386 describe surgical devices which are adapted to support a pre-tied knotted loop of suture for suturing or ligating tissue, particularly during procedures where the tissue desired to be manipulated is difficult to access.

More recently, instrumentation has been developed for facilitating the placement of knots particularly during minimally invasive surgical procedures. In particular, U.S. Pat. No. 5,320,629 discloses the formation of a pre-tied knotted loop of suture, and the placement of the pre-tied knotted loop on a surgical device for facilitating the tightening of the loop to approximate tissue during endoscopic surgical procedures. German Pat. No. 912619 also discloses a device similar to that disclosed in the '629 patent.

Although the art of surgical knots is well developed, and surgical devices for facilitating the placement of tightened knots from a pre-tied knotted loop of suture have also been developed for application at remote surgical sites, there are problems which still need to be addressed. In particular, in those surgical procedures where access to the site is limited, for example during minimally invasive procedures such as endoscopic surgical procedures, the knots can be difficult to deploy. Frequently, the knots which can be deployed are routinely slip knots having poor knot security. If knot security is poor, then the approximated tissue may not be held for a sufficient period of time to promote adequate wound healing. Additionally, during minimally invasive procedures, the pre-tied knotted loops of suture which have been described in the prior art devices can be difficult to efficiently tighten for final deployment.

Therefore, in minimally invasive surgical procedures where access to the surgical site is limited, what is needed is an assembly for facilitating the formation of a surgical knot. The assembly should be relatively simple in construction and should be compatible with a partially tied surgical knot. The assembly should facilitate the conversion of the partially tied knot into a fully formed knot which can provide a consistently strong knot security each time the knot is placed to enable even an inexperienced surgeon to confidently and efficiently place a secure suture knot. Additionally, it would be desirable if it were possible to easily retrofit the assembly onto various surgical instruments, particularly endoscopic instruments, for ease of use of the assembly to place surgical knots. Finally, it would be helpful if it were possible to reload the assembly with a second partially tied knot following deployment of the first knot so that the assembly can be used to place multiple knots.

SUMMARY OF THE INVENTION

The invention is a suture cartridge assembly. The assembly comprises a suture filament which is formed into a partially tied surgical knot, a core tube and a suture cartridge.

The suture filament has proximal and distal ends. The filament is formed into a partially tied surgical knot for facilitating the fastening of bodily tissue. The knot has a first loop formed between the proximal and distal ends of the suture filament. The knot also has a plurality of knot loops formed about the first loop so as to form a common loop core.

The partially tied knot is secured to the core tube, and the suture cartridge contains a tube slot for receiving the core tube.

The incorporation of a suture cartridge containing a slot to receive the partially tied knot secured about the core tube significantly facilitates the formation of a completed non-slip knot from the partially tied knot. The suture cartridge and core tube are easy to make because each requires few component parts. The partially tied knot can be readily secured to the core tube, and the suture cartridge can readily receive the core tube. Therefore, the component parts of the assembly of this invention are not only easy to construct, but also easy to assemble together. The assembly can facilitate converting the partially tied knot into a fully formed knot because the assembly can be retrofitted onto various surgical instruments, including endoscopic instruments used in minimally invasive surgery. Further, because of the simple construction of the assembly and the ease with which the components of the assembly can be assembled, it is straightforward to reload the assembly with a second partially tied knot following deployment of a first knot and removal of the first knot from the cartridge. When used in this manner, the assembly can be retrofitted onto various surgical instruments to facilitate the placement of multiple knots in multiple surgical procedures.

The suture cartridge assembly of this invention can be used in any surgical procedure where it is necessary or desirable to place surgical knots for fastening bodily tissue. Therefore, the suture cartridge assembly will find uses in a whole host of applications, including conventional open

BRIEF DESCRIPTION OF THE PREFERRED EMBODIMENTS

FIGS. 1–6 illustrate how a partially tied surgical knot can be made from a length of suture filament. The partially tied knot thus formed can be used in the practice of the various embodiments of this invention.

Figure 1:
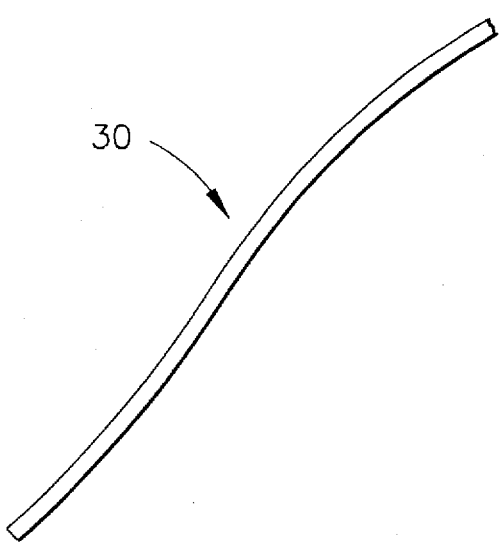
FIGS. 1–6 are perspective views illustrating the sequence of steps for forming a partially tied knot from a length of suture filament.

The suture filament 30 shown in FIG. 1 can be composed of any suture material currently used or hereafter developed. The suture filament may be a monofilament suture or a multifilament, braided suture. The suture filament, regardless of construction, may be non-absorbable or bioabsorbable, depending on the particular application for which the suture is being used to fasten tissue.

The length of suture filament 30 has proximal and distal ends, 31 and 32, respectively. Adjacent the proximal end, there is a proximal length 33 of suture filament. Correspondingly, adjacent the distal end of the suture filament, there is a distal length 34 of the suture filament.

Figure 2:
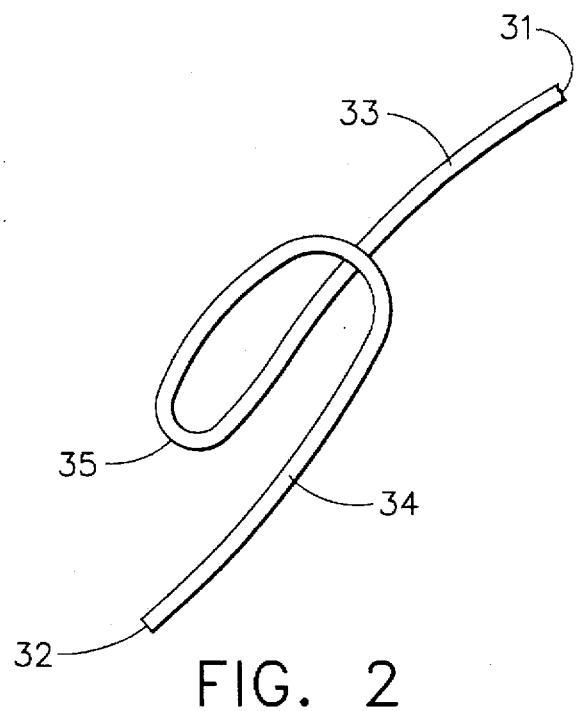
Figure 3:
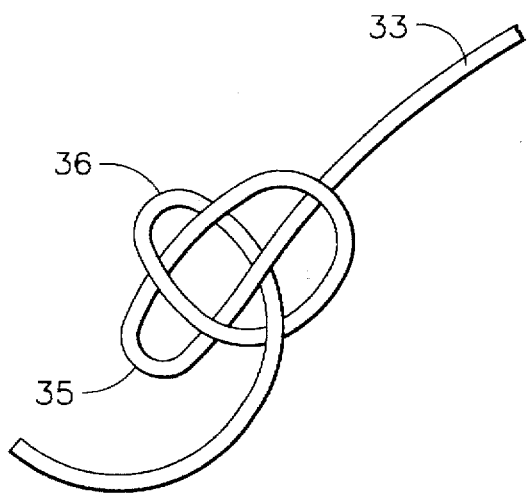
Figure 4:
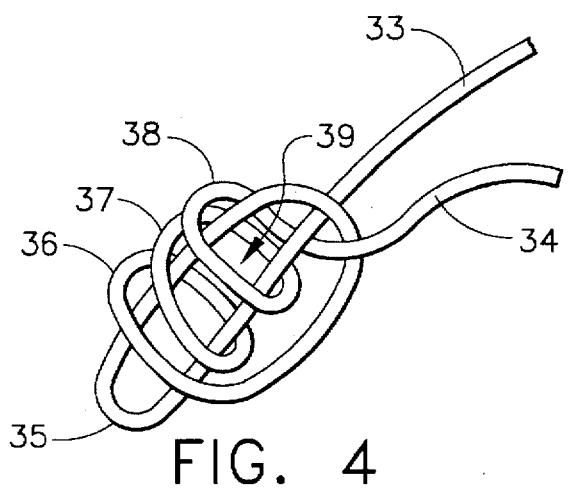

As shown in FIG. 2, a first loop 35 is formed by manipulating the distal length 34 of the suture filament. Now looking at FIG. 3, while the proximal length 33 of the suture filament remains fixed, the distal length is manipulated to form a second loop 36 wrapped generally transversely around the first loop 35. Third and fourth loops, 37 and 38, respectively, are likewise formed about the first loop as depicted in FIG. 4. The second, third and fourth loops are generally parallel to each other and are oriented generally transversely to the first loop. For purposes of describing this invention, these loops may be referred to collectively as the "knot loops". The number of knot loops may vary depending on the particular application for which the knot is used. In the illustrated embodiment, the second, third and fourth loops together form a common loop core 39 which receives the first loop 35.

Figure 5:
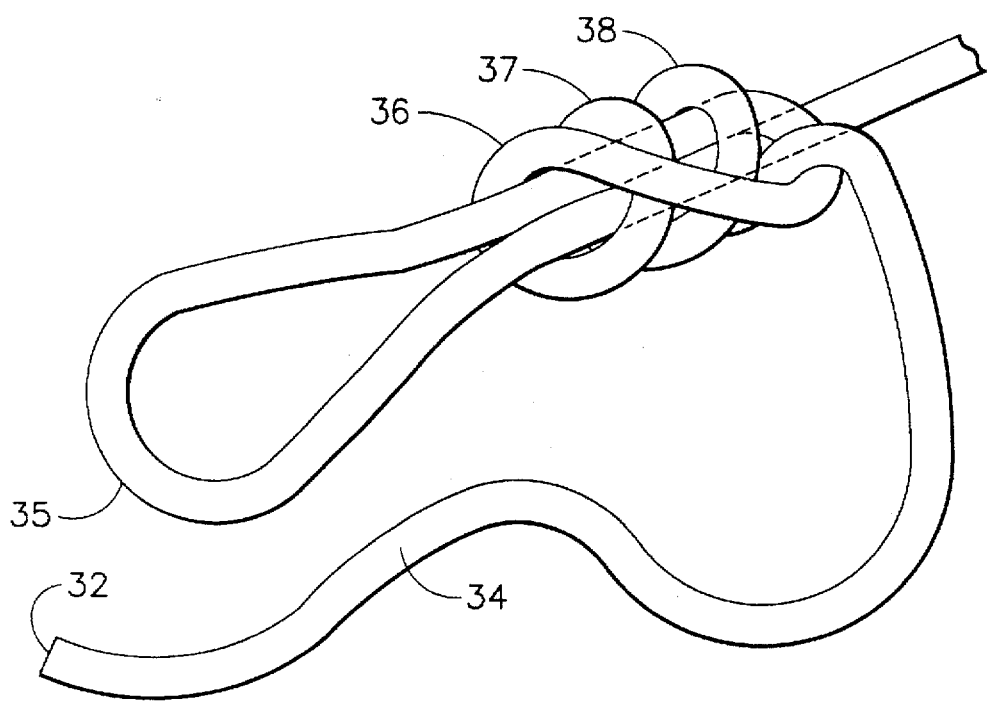

Reviewing FIG. 5, the loosely formed knot is tightened by applying tension on the distal length 34 of the suture filament. In so doing, the second, third and fourth loops tighten down on the first loop, and thus the first loops is securely received in the common loop core.

Figure 6:
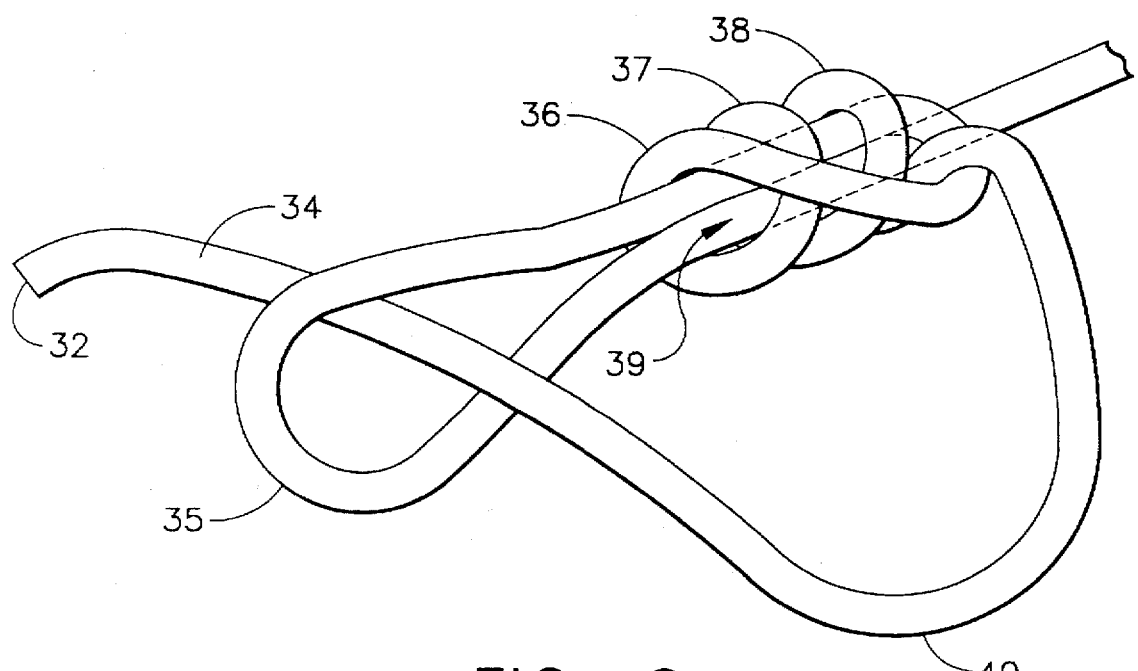

As depicted in FIG. 6, a tissue-fastening loop 40 can be formed by passing the distal end 32 and the distal length 34 of the suture filament through the first loop 35.

Figure 7:
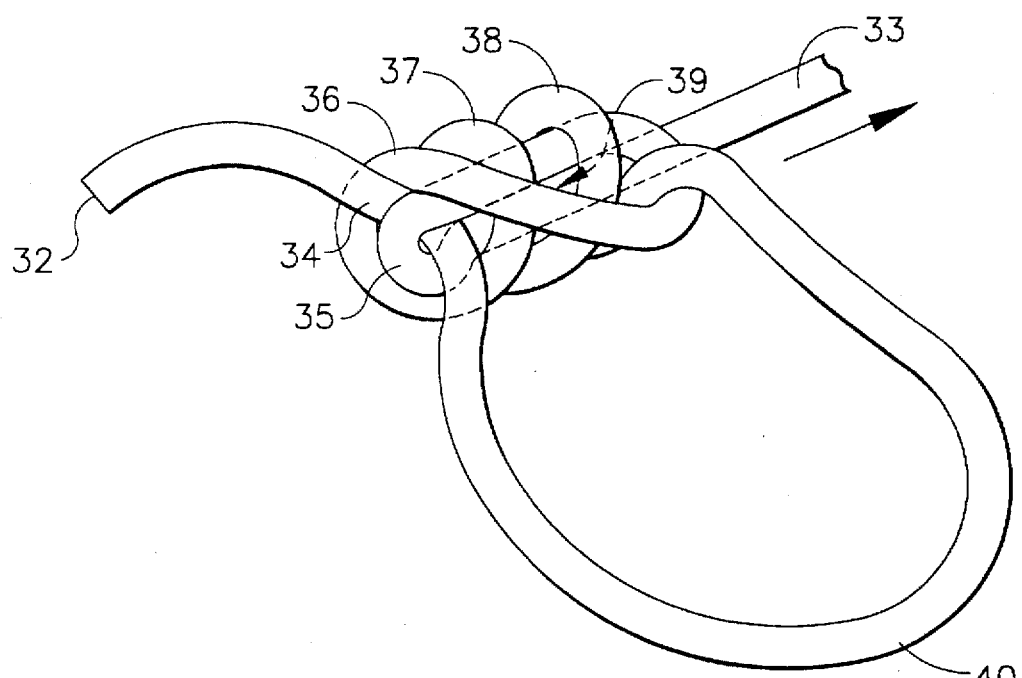
FIGS. 7–8 are perspective views of a preferred embodiment of the invention illustrating the steps to convert the partially tied knot depicted in FIG. 6 into a non-slip surgical knot.

To form the knot represented by a first embodiment of this invention, the partially tied knot of FIG. 6 is taken, and tension on the proximal length 32 of the suture filament is applied in the proximal direction as indicated by the arrow in Figure 7. To facilitate forming the knot, the surgeon ideally holds his fingertips against the proximal side of the knot loops while tension is applied to the proximal length 32 of the suture filament. Alternatively, as described in the embodiments below, an instrument can be used to hold the knot loops in place. As tension is applied, the first loop 35 begins to be pulled through the common loop core 39 of the knot. When the first loop has sufficiently diminished in size from that shown in FIG. 6, it snares the distal length 34 of the suture filament. With continuing proximal tension on the proximal length of the suture filament, the first loop and the distal length of filament are pulled through the common loop core 39. When the first loop and distal length of filament emerge from the fourth loop 38, an audible "clicking" sound will alert the user that the completed knot has been formed.

Although the partially tied knot illustrated in FIG. 6, often referred to as a "blood" knot, is the preferred partially tied knot for conversion into the fully formed, non-slip knot of this invention, other slip knots described in the literature can be used. The key characteristic for the acceptability of other partially tied knots is a common loop core (exemplified in FIG. 6 as common loop core 39) allowing passage of suture filament through the core. See, for example, *The Encyclopedia of Knots and Fancy Ropework*, R. Graumont and J. Hensel, Fourth Edition, Cornell Maritime Press. Suitable partially tied knots are shown in this book as numbers 102, 185, 227 and 349 on pages 71, 83, 87 and 102, respectively.

Figure 8:
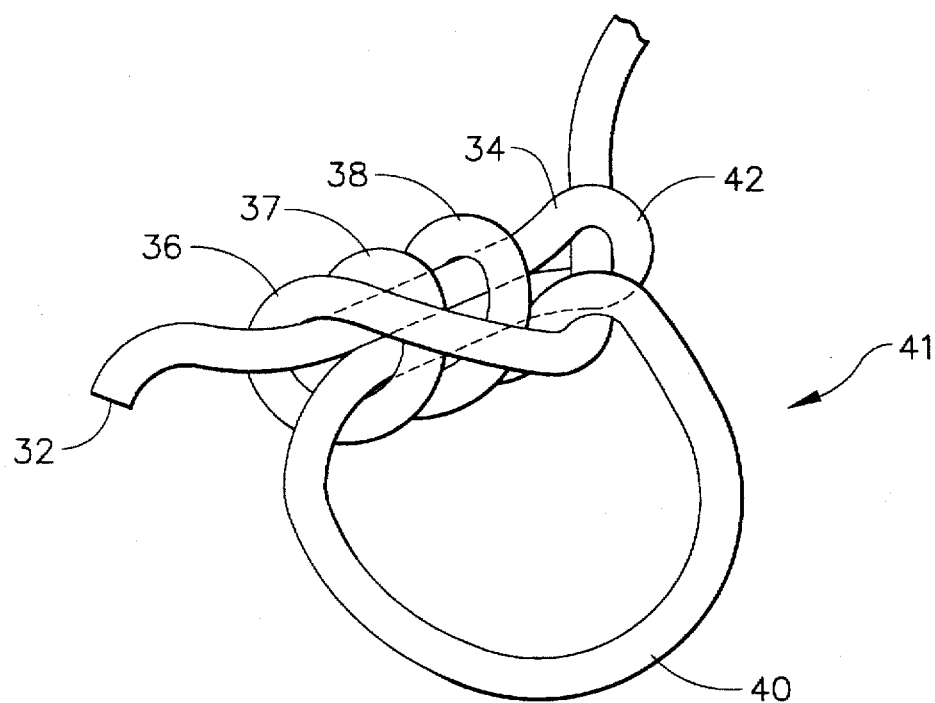

As depicted in FIG. 8, the completed surgical knot of this invention is a non-slip knot 41. The first loop has been eliminated, and a distal loop 42 positioned adjacent to the fourth loop 38 is formed from a portion of the distal length of the suture filament. The tissue loop 40, which is used to fasten tissue, consequently becomes rigidly fixed and secure. Tension applied to the loop 40 due to the tendency of the fastened tissue to expand or pull apart may result beneficially in further tightening of the non-slip knot.

Figure 9:
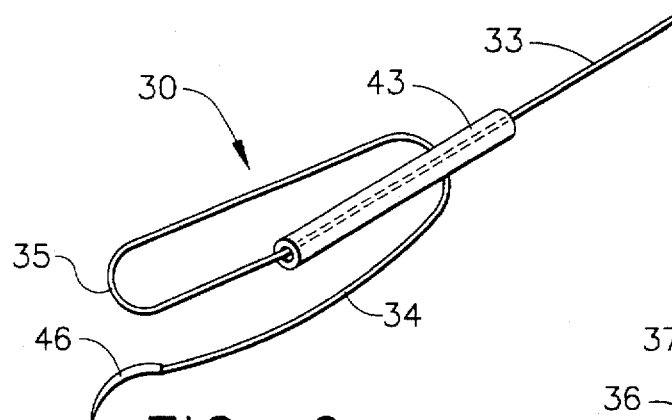
FIGS. 9–10 are perspective views illustrating the formation of the partially tied knot of FIG. 6, which includes a surgical needle attached to the suture filament, about a core tube.
Figure 10:
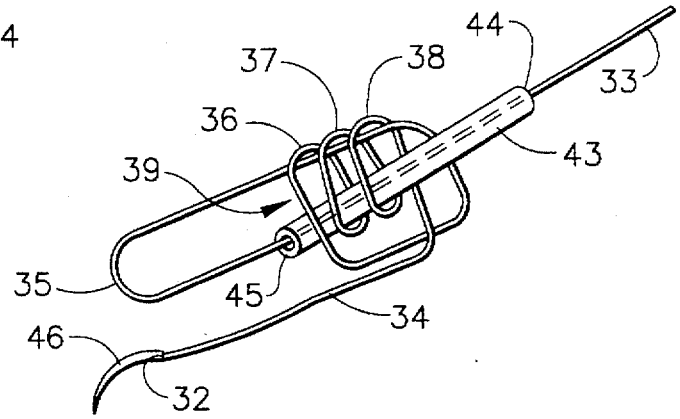

Referring to FIGS. 9 and 10, there is shown the formation of the partially tied knot depicted in FIGS. 1–6, formed about a core tube 43. The core tube facilitates the placement of the partially tied knot adjacent tissue desired to be fastened, as well as the conversion of the partially tied knot into the completed non-slip knot shown in FIG. 8. The core tube has proximal and distal ends, 44 and 45, respectively. A surgical needle 46 is attached to the distal end 32 of the surgical filament. The proximal length 33 of the filament is passed through the core tube. The length of suture filament exceeds the length of the core tube so that the proximal length of the suture filament may extend from the proximal end 44 of the core tube. Additionally, a sufficient amount of suture filament represented by its distal length 34 exits the distal end of the core tube so that it is possible to form the partially tied knot about the distal end 45 of the core tube. The first loop 35 and the subsequent knot loops represented by the second, third and fourth loops, 36, 37 and 38, are formed about the distal end of the core tube. Once formed, tension is applied to the distal length of the filament to tighten the knot loops about the distal end of the core tube.

Figure 11:
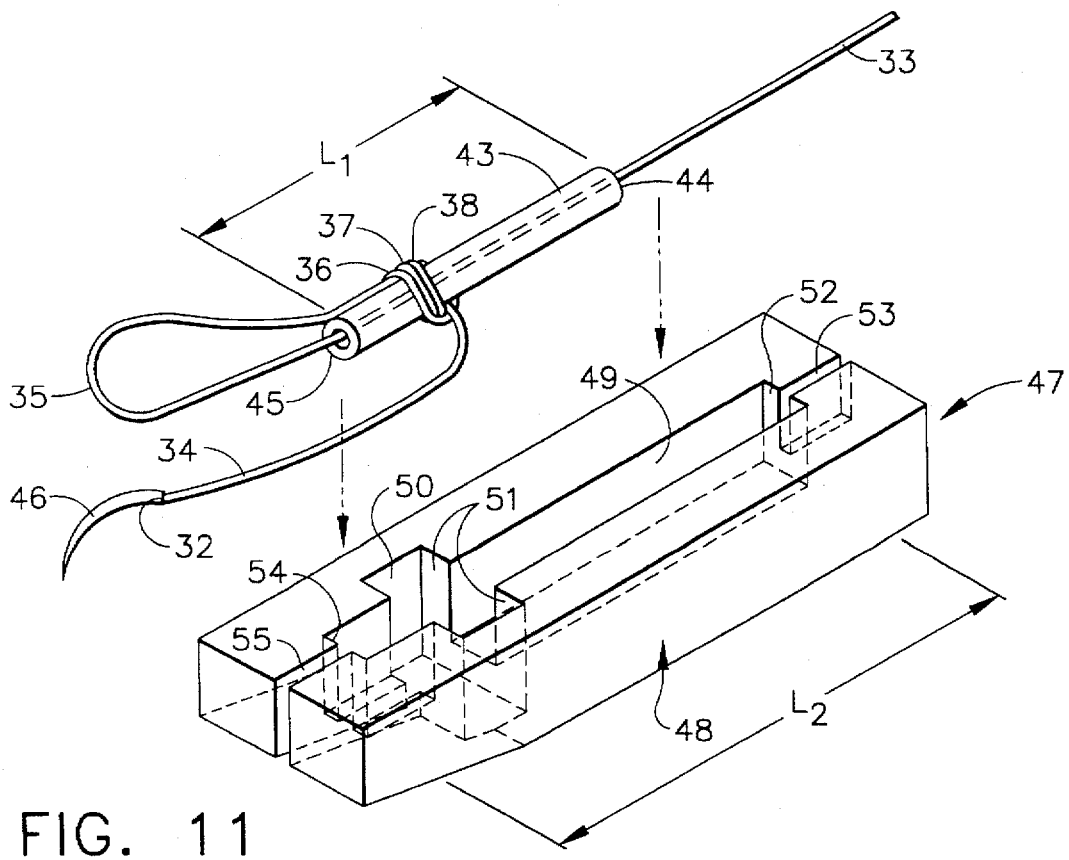
FIG. 11 is an exploded perspective view of another preferred embodiment of the invention illustrating the partially tied knot of FIG. 6 formed about the core tube depicted in FIGS. 9–10, in combination with a suture cartridge.

In another embodiment of the invention, the partially tightened knot formed about the core tube can be loaded into a suture cartridge 47 as illustrated in FIG. 11. The suture cartridge has an elongated body 48. A tube slot 49 for receiving the core tube 43 is embedded in the body of the cartridge. The body also contains a knot recess 50 which has a pair of stripping shoulders 51. Extending from a proximal edge 52 of the tube slot in a proximal direction is a filament slot 53. Correspondingly, extending from a distal edge 54 of the tube slot toward a distal end of the cartridge body is a loop slot 55. The length of the core tube, designated as $L_1$ in FIG. 11, is less than the length of the tube slot, designated as $L_2$ in FIG. 11.

Figure 13:
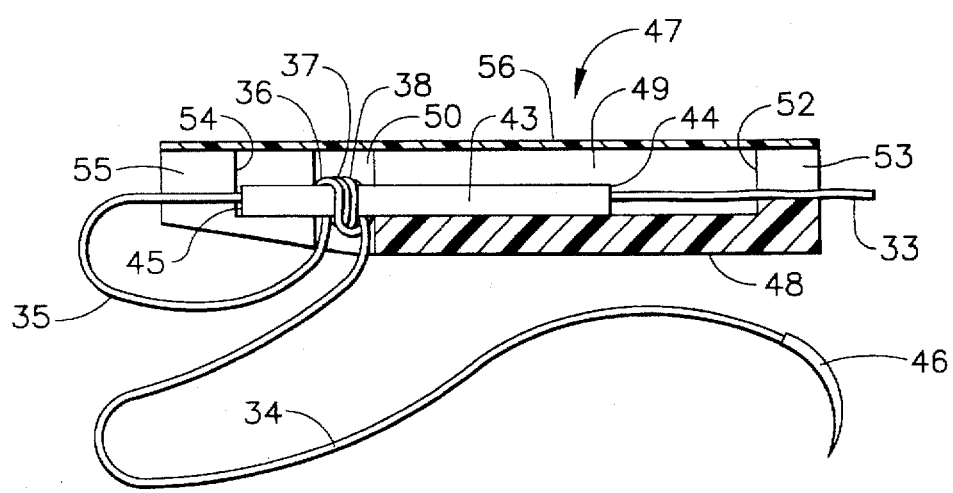
FIG. 13 is a section view of the assembly depicted in FIG. 12 taken along line 13—13 of that Figure.

When the partially tied knot is formed about the core tube 43, the knot loops are wrapped about the distal end 45 of the core tube. The free proximal end of the suture filament extends from the proximal end 44 of the core tube. The first loop 35 of the partially tied knot extends from the distal end of the core tube. When the core tube is loaded into the tube slot 49 of the cartridge body, the knot loops sit inside the knot recess and abut the stripping shoulders of the knot recess. A portion of the proximal length 33 of the suture filament rests in the filament slot 53 embedded in the body of the cartridge, and the remaining portion of the proximal length of the suture filament extends from the proximal end of the cartridge body. Correspondingly, the first loop 35 of the partially tied knot and the distal end 34 of the surgical filament are received in the loop slot 55. A substantial portion of the first loop and the distal length of suture filament extend outside of the cartridge body. In its original position as best illustrated in FIG. 13, the distal end 45 of the core tube is adjacent the distal edge 54 of the tube slot. Since the tube slot 49 has a length greater than that of the core tube 43, the core tube is capable of sliding proximally toward the proximal edge 52 of the tube slot. In this position, the knot is trapped in recess 50. The surgeon can then easily manipulate needle 46 and suture filament 34 without danger of prematurely deploying the knot.

Figure 12:
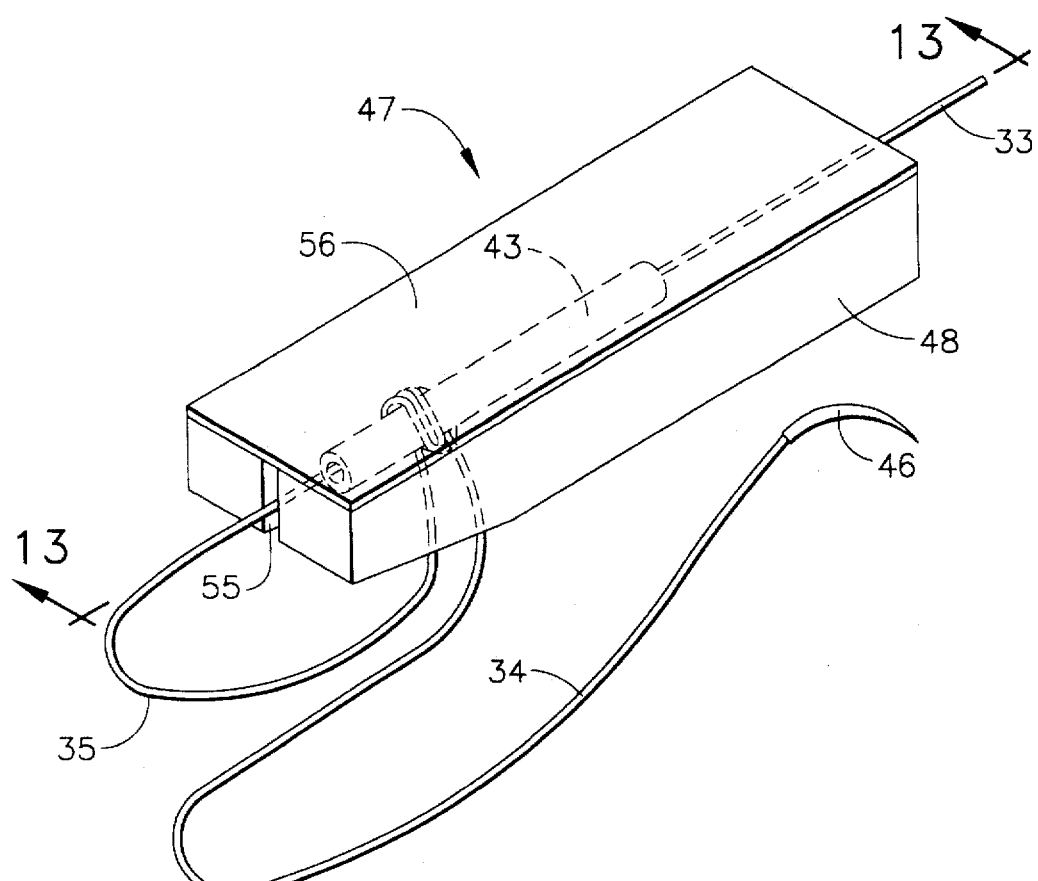
FIG. 12 is a perspective view in assembly of the combination depicted in FIG. 11, where the suture cartridge has a cartridge top.

When the core tube is loaded into the tube slot within the body of the cartridge, a cartridge top 56 can be mounted onto the cartridge body 48 as shown in FIG. 12. When the cartridge top is mounted, the core tube 43 is fully enclosed within the cartridge.

Figure 14:
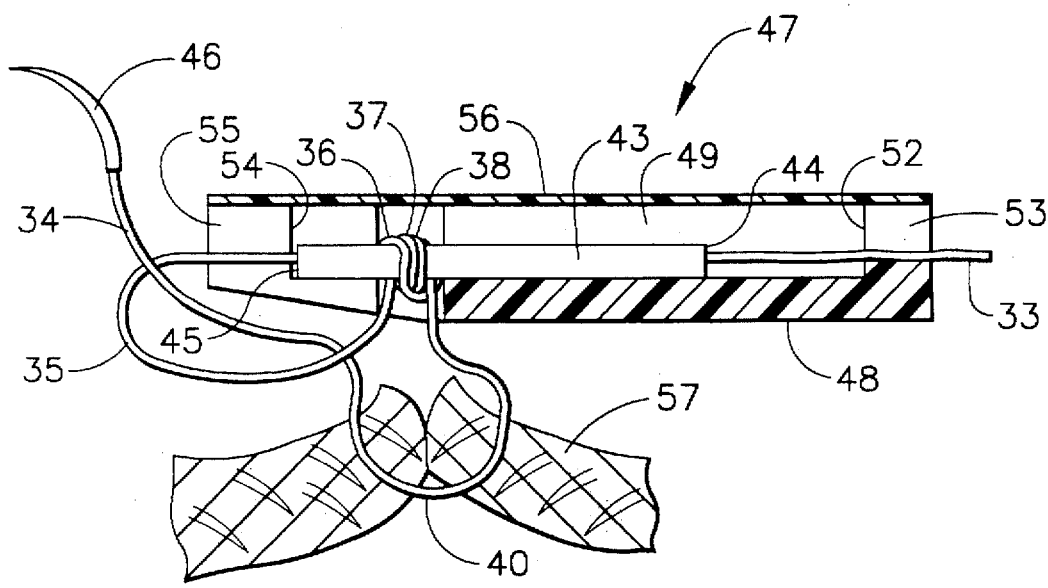
FIGS. 14–15 are section views of the assembly depicted in FIG. 13, including a fragmentary section of tissue, illustrating the use of the partially tied knot to fasten tissue and the steps necessary to form the completed non-slip surgical knot to securely fasten the tissue.
Figure 15:
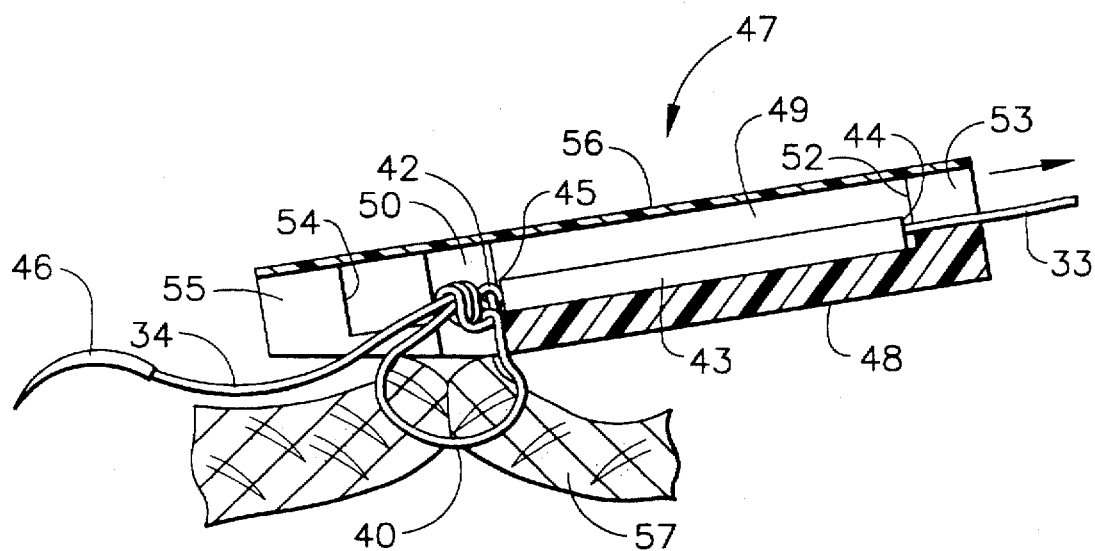

With the core tube fully enclosed within the suture cartridge, the partially tied knot wrapped about the core tube can be deployed to fasten desired bodily tissue as illustrated in FIGS. 14–15. The first step is to position the suture cartridge 47 adjacent bodily tissue 57 desired to be fastened. Next, the surgical needle 46 is passed through the tissue, and into and through the first loop 35 to form the tissue loop 40. The size of the tissue loop is adjusted to provide the appropriate tension on the opposed tissue sections of the bodily tissue 57 desired to be fastened; once the knot is completed to from the non-slip knot, the tissue loop becomes rigidly fixed and further adjustment is unavailable. When the tissue loop 40 is formed and appropriately sized, proximal tension is applied to the proximal length 33 of the suture filament in the direction of the arrow as depicted in FIG. 15. The completed knot is formed when sufficient tension is felt or applied to the proximal length 33.

Advantageously, when tension is applied to the proximal length 33 of the filament, the first loop is pulled and eventually applies a proximal force against the distal end 45 of the core tube 43, causing it to slide proximally as shown in FIG. 15. Since the knot loops abut against the stripping shoulders in the knot recess 50, the knot loops remain stationary even though the core tube slides proximally. When the core tube slides to a position where it is adjacent the proximal edge 52 of the tube slot 49, the knot loops are stripped from the distal end 45 of the core tube. The knot is then fully formed, and the user can remove the cartridge top 56, cut the remaining proximal and distal lengths of suture filament, and remove the core tube. Alternatively, the proximal and distal lengths of suture filament can be exposed without removing cartridge top 56 by releasing the tension on proximal length 33 and pulling the cartridge proximally, thus allowing a portion of the proximal and distal lengths of suture filament contained in the core tube 43 to extend distally from recess 50.

The suture cartridge 47 is advantageous because it is readily adaptable to conventional open and endoscopic instruments, and thus readily facilitates the formation of the knot. The suture cartridge may be disposable, or it can be used on multiple patients. When used on multiple patients, a plurality of disposable core tubes, including the partially tied knot wrapped about the tube, can be loaded serially into the suture cartridge to provide for the placement of numerous surgical knots to fasten tissue using a single suture cartridge.

Figure 21:
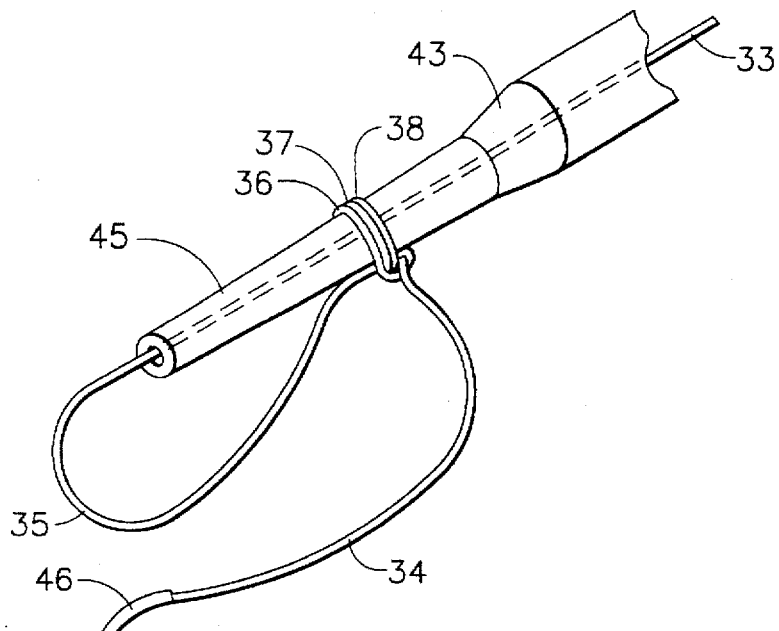
FIGS. 21–23 illustrate the use of the partially tied knot depicted in FIG. 6 formed about a tapered core tube to fasten tissue when the partially tied knot is converted to a completed, non-slip surgical knot.
Figure 22:
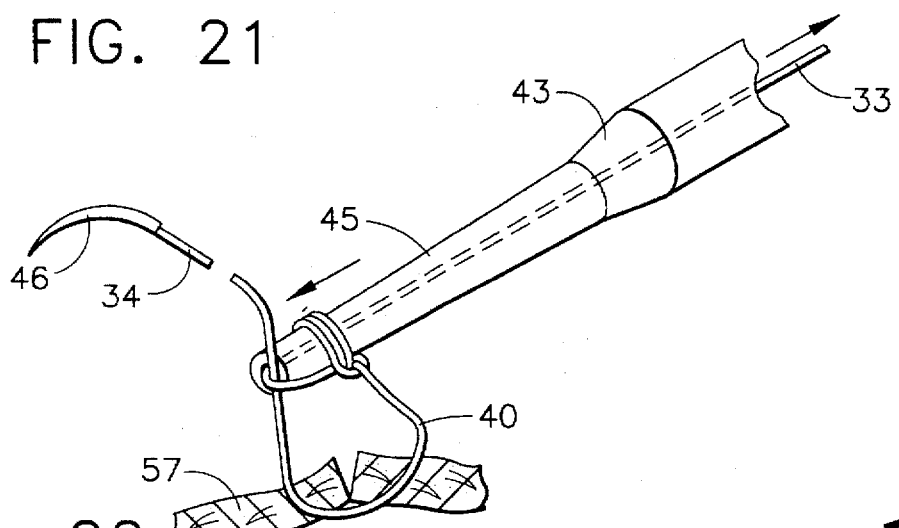
Figure 23:
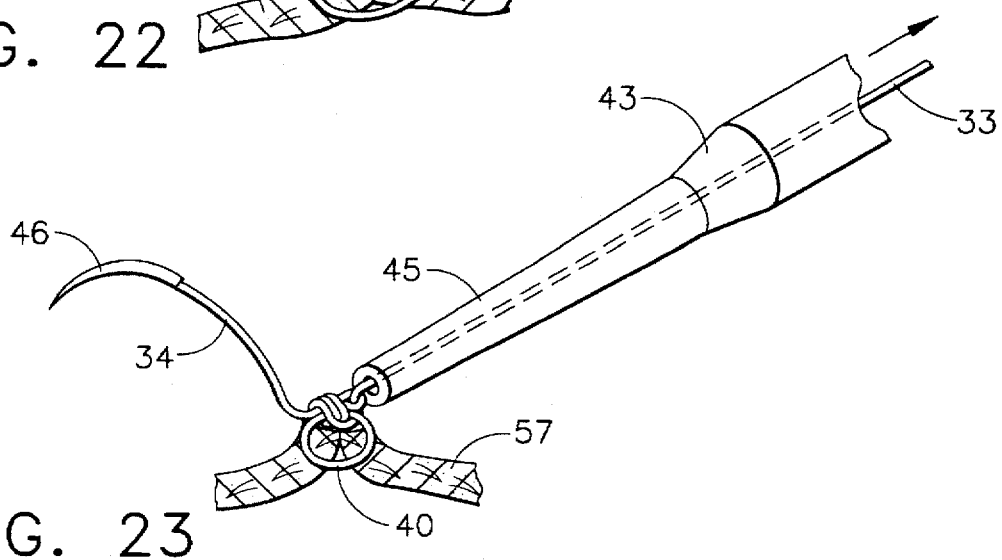

In another embodiment of the invention, the partially tied knot is wrapped about the core tube to facilitate the conversion of the knot to the completed, non-slip knot to fasten tissue. This similar embodiment is illustrated in FIGS. 21–23. The one key difference between what is shown here and that illustrated in FIGS. 9–15 is that the core tube has a tapered distal end. For convenience, the same numbers have been used to identify component parts in FIGS. 21–23 as those used in FIGS. 9–15.

Figure 16:
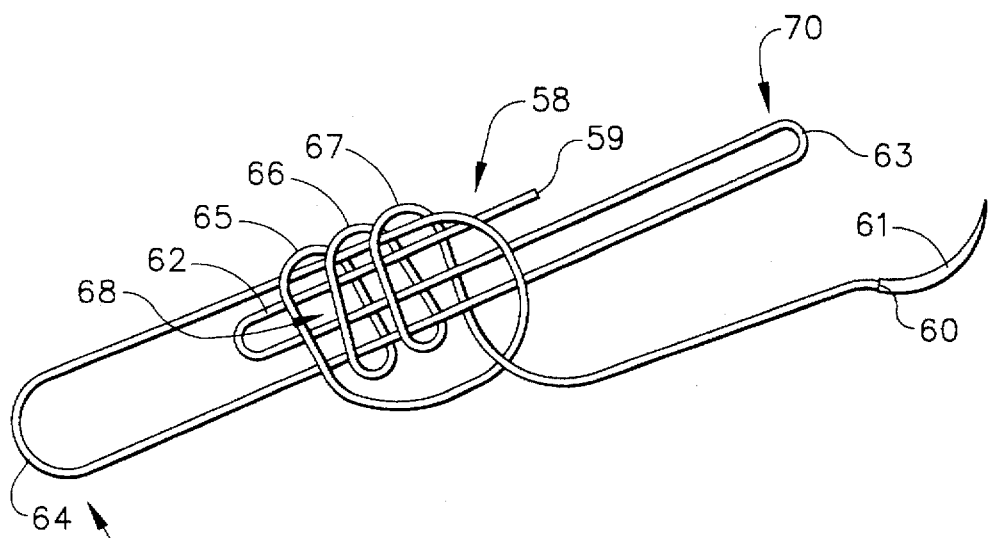
FIGS. 16 and 17 are perspective views of yet another preferred embodiment of the invention depicting the formation of a different partially tied surgical knot from a length of suture filament.
Figure 17:
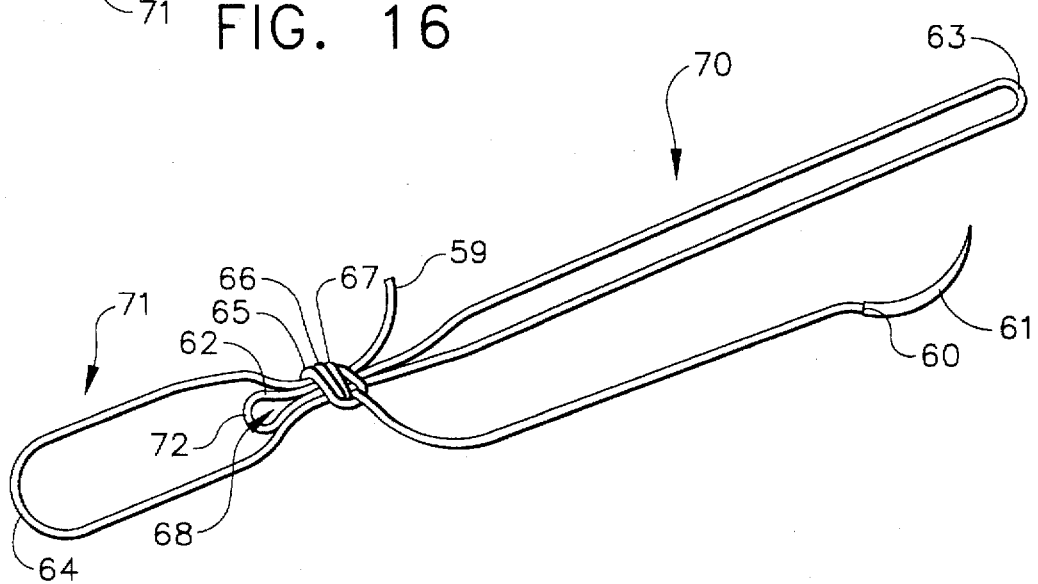

In yet another embodiment of this invention, a partially tied surgical knot is illustrated in FIGS. 16–17. The knot is made from a suture filament 58 which has a proximal end 59 and a distal end 60. A surgical needle 61 is attached to the distal end. The distal end of the filament is manipulated to form the knot while the proximal end of the filament is held stationary. A core loop 62, proximal loop 63 and first loop 64 are initially formed. The proximal loop is at a first end 70 of the knot, and the first loop is at an opposite end 71 of the knot. The core loop is situated between the first and opposite ends of the knot. Knot loops, in the preferred embodiment consisting of second, third and fourth loops, 65, 66, and 67, are formed about the proximal loop 63 and the first loop 64. The knot loops together form a common loop core 68. The core loop is positioned within the common loop core. When tension is applied to the distal end of the surgical filament while the proximal end of the knot loops is supported, the knot loops are tightened. The knot loops are tightened about the first loop, proximal loop and core loop. When tightened, as shown in FIG. 17, the first loop, core loop and proximal loop are securely received in the knot loops, and the partially tied knot is formed.

Referring specifically to FIG. 17, the core loop 62 has a free proximal end 69 extending from the common loop core 68 toward the first end 70 of the knot. The core loop has a loop end 72 which extends from the common loop core in an opposite direction toward the opposite end 71 of the knot. The loop end 72 of the core loop 62 is disposed inside the first loop 64.

The partially tied knot of FIG. 17 can be converted to a completed non-slip knot when axial tension is applied to the proximal loop in the proximal direction while the proximal end of the knot loops is supported. In a manner similar to the deployment of the knot best illustrated in FIGS. 1–8, the knot is converted when the first loop is pulled through the common loop core to form a distal loop. Advantageously, when tension is applied on the proximal loop, not only is the first loop pulled through the common loop core, but also the core loop is pulled through as well. This provides an advantage because the core loop creates a sufficient space represented by the common loop core to enhance the ease of passage of the first loop through the common core to form the completed knot. Easier passage reduces the amount of tension which is needed to be applied to the proximal loop to form the completed knot, and therefore increases the degree of control of the user when the knot is being deployed.

Figure 18:
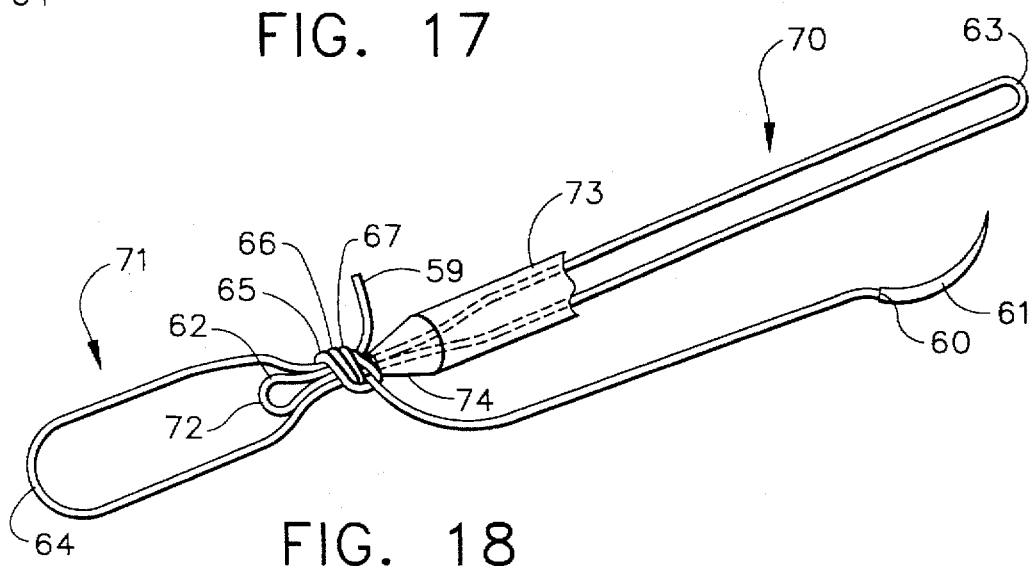
FIG. 18 is a perspective view of the partially tied knot depicted in FIG. 17 formed about a stripping tube.
Figure 19:
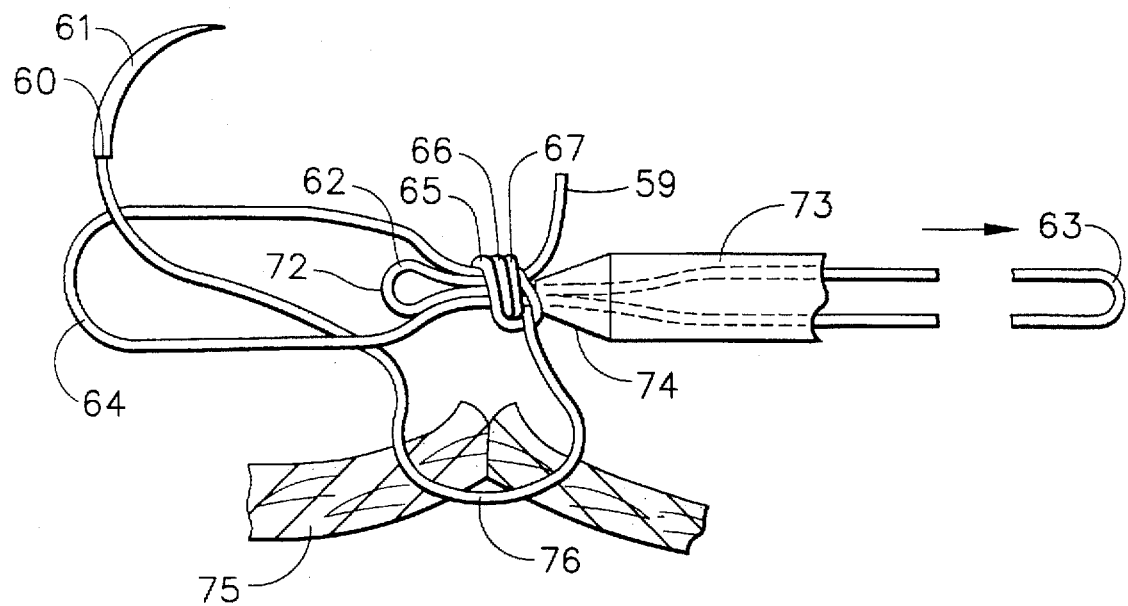
FIGS. 19–20 are side elevation views illustrating the use of the assembly depicted in FIG. 18 to form a completed, non-slip surgical knot to fasten tissue.
Figure 20:
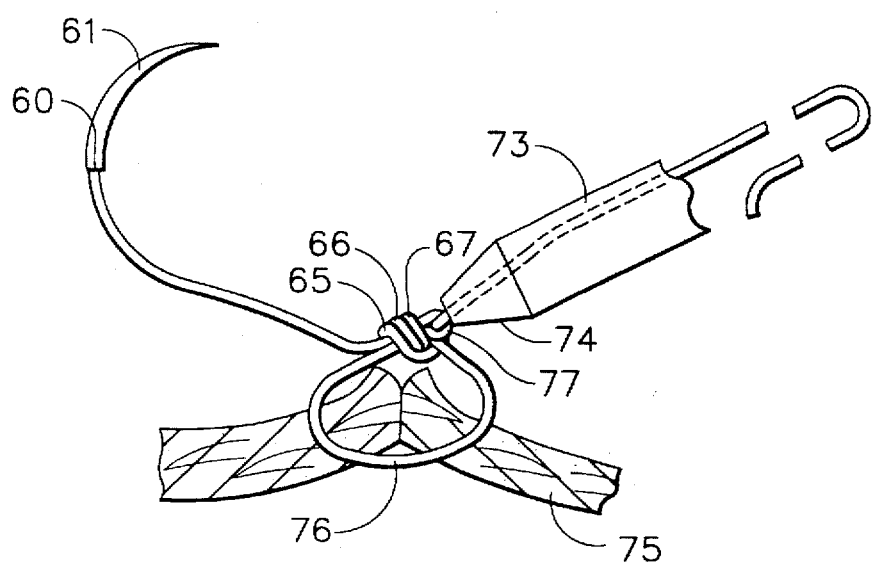

FIGS. 18–20 illustrate the use of the knot depicted in FIG. 17 to fasten tissue, where the knot is deployed in combination with a stripping tube 73. When the partially tied knot of FIG. 17 is formed, the proximal loop 63 is passed through the stripping tube. A portion of the proximal loop extends from a proximal end of the stripping tube. The proximal loop is passed through the stripping tube until the knot loops abut against the distal end of the stripping tube. Significantly, the stripping tube has a tapered distal end 74. The core loop and the first loop extend away from the tapered distal end of the tube. The opening at the distal end of the tube is smaller in diameter than the diameter of the knot loops. Consequently, when tension is applied on the proximal loop in the proximal direction, the knot loops will not pass into the stripping tube.

The conversion of the partially tied knot to the completed knot is performed in a manner substantially similar to that described in the previous embodiments.

Referring now to FIGS. 19–20, the stripping tube 73 is positioned adjacent bodily tissue 75 desired to be fastened. The surgical needle 61 is drawn through the tissue. A tissue loop 76 is formed when the surgical needle and distal end of the filament are fed through the first loop 64. Again, it is important to adjust the size of the tissue loop to provide for appropriate tensioning of the fastened tissue before the knot is fully deployed. When the desired tissue loop is formed, tension on the proximal loop 63 is applied in the proximal direction as indicated by the arrow in FIG. 19 to pull the core loop 62 and the first loop 64 through the common loop core. When the first loop emerges from the fourth knot loop 67, the distal loop 77 is formed, and the completed, non-slip knot has been created.

The different embodiments of this invention are representative of the preferred embodiments of the invention. These embodiments are merely illustrative. The scope of the invention should not be construed to be limited by these embodiments, or any other particular embodiments which may come to mind to those skilled in this art. Instead, the reader must refer to the claims which appear below to determine the scope of the invention.

What is claimed is:

1. A suture cartridge assembly comprising:

a) a suture filament having proximal and distal ends, said filament being formed into a partially tied surgical knot for facilitating the fastening of bodily tissue, said knot having a first loop formed between the proximal and distal ends of said suture filament, and a plurality of knot loops formed about said first loop so as to form a common loop core;

b) a core tube wherein said partially tied knot is secured to said tube; and c) a suture cartridge containing a tube slot for receiving said core tube, said tube slot having a proximal edge and a distal edge, and said suture cartridge containing a knot recess for receiving said knot loops, said knot recess embedded in said tube slot between the proximal and distal edges of said tube slot.

2. The suture cartridge assembly of claim 1 further comprising a surgical needle attached to the distal end of said suture filament.

3. The suture cartridge assembly of claim 1 wherein said suture filament is initially passed through said core tube, and said partially tied surgical knot is then formed about said tube wherein the proximal end of said suture filament extends from a proximal end of said core tube, said first loop extends from a distal end of said core tube, and said knot loops are wrapped around said core tube.

4. The suture cartridge assembly of claim 3 wherein said suture cartridge contains a loop slot for receiving a portion of said first loop, and a filament slot for receiving a portion of the proximal end of said suture filament.

5. The suture cartridge assembly of claim 4 wherein said first loop extends from a distal end of said suture cartridge, and the proximal end of said suture filament extends from a proximal end of said suture cartridge.

6. The suture cartridge assembly of claim 5 wherein said core tube has a tube length, said tube slot of said suture cartridge has a slot length, and said slot length is greater than said tube length.

7. The suture cartridge assembly of claim 6 wherein said knot recess has a pair of stripping shoulders, and said knot loops abut said shoulders.

8. The suture cartridge assembly of claim 7 wherein when axial tension is applied on the proximal end of said suture filament so as to pull said first loop through said core tube, said core tube slides proximally in said tube slot while said knot loops remain stationary abutting said stripping shoulders, and said knot loops are stripped from said core tube.

9. The suture cartridge assembly of claim 8 wherein said suture cartridge has a cartridge top, and when said core tube is loaded into said tube slot, and said cartridge top is mounted onto said suture cartridge, said core tube is fully enclosed in said suture cartridge.

* * * * *